United States Patent [19]

Daglow et al.

[11] Patent Number: 5,070,605
[45] Date of Patent: Dec. 10, 1991

[54] METHOD FOR MAKING AN IN-LINE PACEMAKER CONNECTOR SYSTEM

[75] Inventors: Terry D. Daglow, Little Canada; Richard D. Sandstrom, Scandia, both of Minn.

[73] Assignee: Medtronic, Inc., Minneapolis, Minn.

[21] Appl. No.: 469,629

[22] Filed: Jan. 24, 1990

Related U.S. Application Data

[62] Division of Ser. No. 184,903, Apr. 22, 1988, Pat. No. 4,934,367.

[51] Int. Cl.⁵ .................... H01R 43/20; H01R 17/18
[52] U.S. Cl. ............................ 29/842; 29/844; 29/854; 128/419 P; 427/2; 427/124; 439/668; 439/699; 439/909; 439/931; 439/933
[58] Field of Search ............ 128/419 P; 439/668, 439/669, 86, 660, 699, 884, 886, 908, 909, 931, 933; 427/2, 123, 124, 404, 126.3; 65/60.4; 29/860

[56] References Cited

U.S. PATENT DOCUMENTS

| | | | |
|---|---|---|---|
| 3,126,596 | 3/1964 | Rector | 29/860 |
| 3,704,163 | 11/1972 | Limbough | 427/404 |
| 4,196,029 | 4/1980 | Privas | 427/123 |
| 4,259,409 | 3/1981 | Arnold | 427/123 |
| 4,469,104 | 9/1984 | Peer-Travarton | 128/419 P |
| 4,487,463 | 12/1984 | Tillotson | 439/660 |
| 4,712,557 | 12/1987 | Harris | 439/669 |
| 4,848,352 | 7/1989 | Pohndorf et al. | 128/419 P |

FOREIGN PATENT DOCUMENTS

| | | | |
|---|---|---|---|
| 413900 | 7/1934 | United Kingdom | 65/60.4 |
| 892801 | 3/1962 | United Kingdom | 439/668 |

OTHER PUBLICATIONS

IBM Technical Disclosure Bulletin, "Sliding Electrical Contact", p. 101, vol. 11, No. 2, Jul. 1968.

Primary Examiner—Michael W. Ball
Assistant Examiner—Francis J. Lorin
Attorney, Agent, or Firm—Reed A. Duthler

[57] ABSTRACT

A connector system for use in coupling an implantable electrical lead to an implantable pulse generator, or other implantable electrical apparatus. The connector system includes a connector pin assembly, typically mounted to the implantable lead and a connector block, typically mounted to the electrical stimulator. The connector block is provided with a lumen, in which a plurality of resilient, elastomeric rings are linearly arranged. The rings are so sized as to frictionally engage a connector pin which is provided with a plurality of conductive pads, each coupled to a conductor within the implantable lead. Certain ones of the elastomeric rings are conductive, and engage with the conductive pads on the connector pin. Others of the rings are nonconductive and act as insulators and fluid seals. The connector pin assembly is also provided with a circumferential groove, which interlocks with the deflectable beam members of a retainer mounted to the connector block. An alternative connector block embodiment employs a metallic spring element to contact conductive areas on the connector pin.

11 Claims, 4 Drawing Sheets

METHOD FOR MAKING AN IN-LINE PACEMAKER CONNECTOR SYSTEM

This is a divisional of copending application Ser. No. 07/184,903 now U.S. Pat. No. 4,934,367 filed on 4/22/88.

BACKGROUND OF THE INVENTION

This invention relates generally to implantable electrical leads and their connector systems, and more particularly relates to connector systems for multiple conductor electrical leads used in conjunction with cardiac pacemakers.

Early implantable electrical leads having multiple conductors tended to have an individual connector pin coupled to each conductor in the electrical lead, and a connector block having a lumen corresponding to each connector pin mounted to the implantable stimulator. Examples of such connector systems are illustrated in U.S. Pat. No. 3,348,548, issued to Chardack, and U.S. Pat. No. 4,144,891, issued to Lysfjord et al. More recently, there has been a trend toward in-line connector systems, which employ a single connector pin having linearly arranged conductive surfaces, mounted to the electrical lead and a connector block having a single lumen containing correspondingly arranged connector surfaces. Such systems are illustrated in EPO Patent No. 0 052 879, issued to Rose, U.S. Pat. No. 4,572,605, issued to Hess, and U.S. Pat. No. 4,603,696, issued to Cross et al. A variety of methods for maintaining electrical contact in such systems have been employed. These include set screws, as illustrated in U.S. Pat. No. 3,908,668, issued to Bolduc, spring members, as illustrated in U.S. Pat. No. 4,445,511 issued to Cowdery et al, collets, as illustrated in U.S. Pat. No. 4,278,093, issued to Lafortune et al, and garter springs or conductive polymer rings as illustrated in U.S. Pat. No. 4,437,474, issued to Peers-Trevarton. A variety of methods of maintaining the physical interconnection of the connector system have also been employed. These include the above-mentioned methods for maintaining electrical contact, and also include bayonet type fittings used on early G.E. pacemakers and locking mechanisms, as illustrated in U.S. Pat. No. 4,540,236, issued to Peers-Trevarton.

SUMMARY OF THE INVENTION

The present invention provides an improved connector system for use in interconnecting cardiac pacing leads or other electrical leads with cardiac pacemakers or other electrical implantable devices. The electrical lead is provided with a connector assembly including a connector pin. One embodiment of the connector pin has conductive paths and dielectric barrier layers printed upon it, similar to a printed circuit board. This provides a pin having multiple conductor surfaces and having a substantially uniform diameter along its length. As such, the mechanical configuration of such connector pins may be substantially identical, whether they include one, two, three or more conductive surfaces. This feature facilitates ready interchange of the leads from one device to another.

The connector block mounted to the pulse generator is provided with a cylindrical lumen, in which a plurality of electrical contacts are located. In one embodiment, the electrical contacts take the form of conductive elastomeric rings, arranged between nonconductive elastomeric rings. The nonconductive rings serve to insulate adjacent ones of the conductive elastomeric rings from one another. All of the elastomeric rings serve as fluid seals, and eliminate the need for sealing rings along the connector pin on the lead.

This configuration of the connector block provides for a flexible, easy to manufacture assembly. By altering the arrangement and number of conductive rings as compared to nonconductive rings, connector assemblies for use with leads having one, two, three or more conductors may easily be fabricated. Typically, the connector assembly is provided with a plurality of bores perpendicular to the lumen. These allow for feedthrough conductors to enter the lumen, making contact with the conductive ones of the elastomeric rings. In this manner, a single connector block molding may serve for a variety of pacemakers or other electrical devices, with connections automatically made only where appropriate, upon installation of the connector block. An alternative embodiment of the connector block employs conductive spring members as electrical contacts.

The connector pin on the lead is retained within the connector block by means of a snap-in lead retainer. The connector assembly on the lead is provided with a circumferential groove which engages with deflectable, curved beams, which snap into the groove on the connector pin. This assembly can be made permanent by the addition of a suture, surrounding the deflectable beams in the area of their contact with the circumferential groove on the connector pin assembly. This eliminates the necessity for set screws or other locking connectors to retain the lead within the pacing system, and is a procedure with which implanters of pacemakers are generally familiar.

DETAILED DESCRIPTION OF THE DRAWINGS

Figure 1:
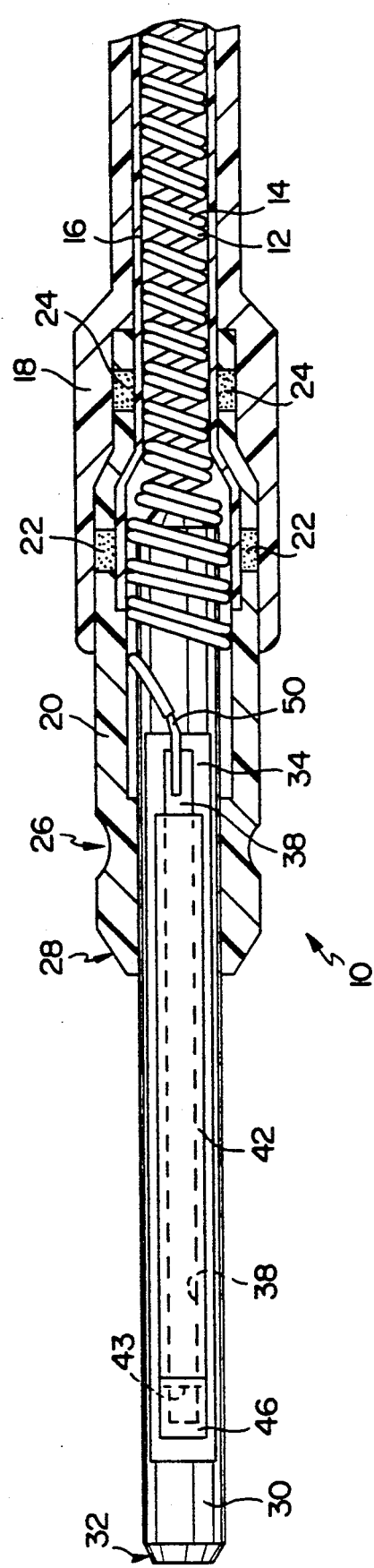
FIG. 1 is a cut-away view of a bipolar connector pin assembly according to the present invention.
Figure 2:
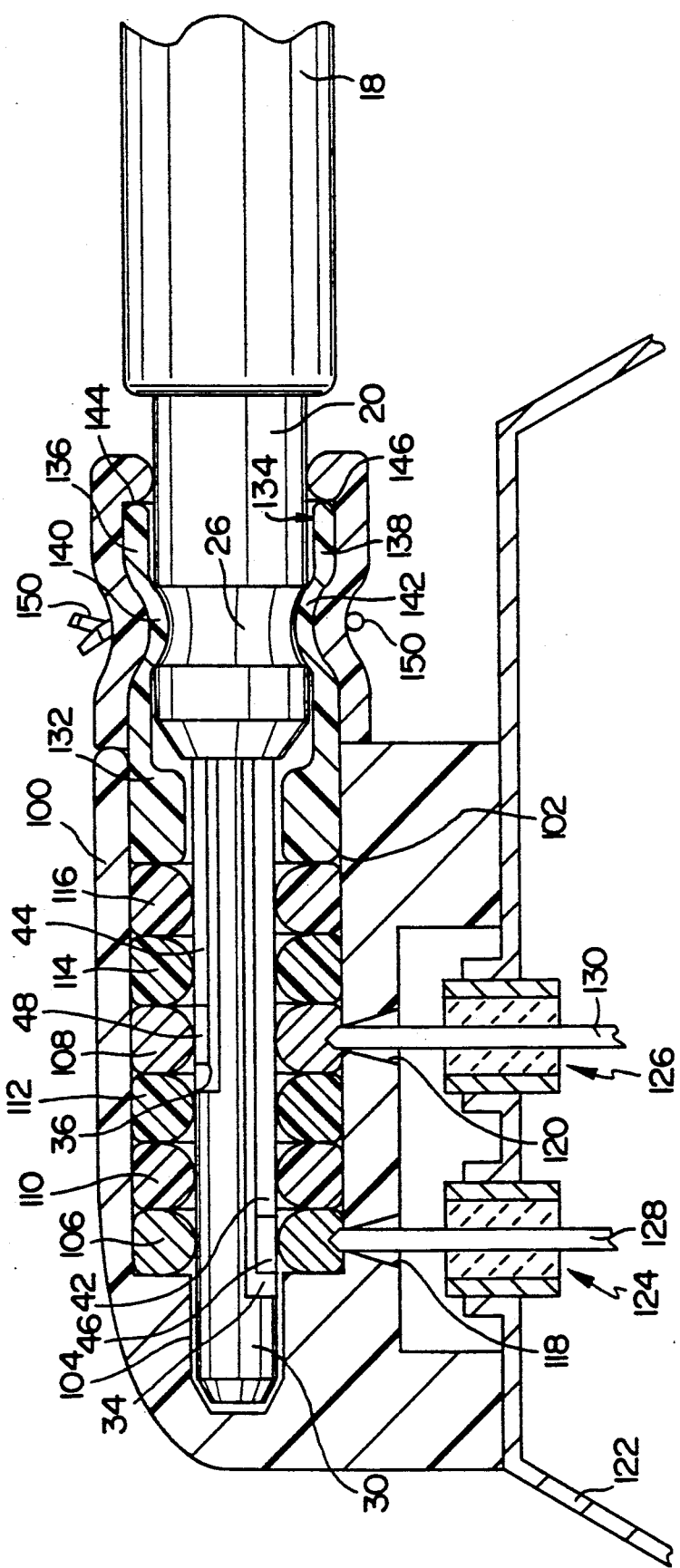
FIG. 2 is a cut-away view of a connector block according to the present invention, in combination with an inserted, bipolar connector pin assembly.

FIG. 1 shows a cut-away view of a lead having a connector assembly 10 according to the present invention. The lead as illustrated is a bipolar lead, employing two mutually insulated electrical conductors 12 and 14, which take the form of a bipolar, bifilar coil. Conductors 12 and 14 are insulated from one another by means of a coating of Tefzel ® polymer or other insulative coating. Conductors 12 and 14 may be fabricated of MP35N alloy or other commonly used conductor materials. In the vicinity of the connector assembly, the outer insulative sheath 16 of the lead is surrounded by a flexible boot 18, which acts as a strain relief. The boot 18 is coupled to a generally tubular member 20, fabricated of plastic, such as Delrin ® plastic, polypropylene, Pellethane ® polyurethane or other similar biocompatible plastic. The boot 18 is coupled to the tubular member 20 and to the outer insulative sheath 16 by means of adhesive 22, 24, located in bores extending through the tubular member 20. This provides both an adhesive connection and a mechanical interlock between the tubular member 20, the outer insulative sheath 16 of the lead, and the strain relief boot 18. Tubular member 20 is provided with a circumferential groove 26, which is used in conjunction with a deflectable beam lead retainer (FIG. 2). The proximal end 28 of tubular member 20 is tapered to facilitate insertion into the connector assembly.

Mounted within tubular member 20 is a generally cylindrical ceramic pin 30. Ceramic pin 30 serves to couple the electrical conductors 12 and 14 to an implantable pacemaker or other electrical device. The proximal end 32 of pin 30 is provided with a taper to facilitate insertion into the connector block.

Connector pin 30 is provided with conductive paths and connector pads by means of sequential deposition of insulative and conductive materials, using procedures typically used to fabricate ceramic hybrid circuits. In this view, only one conductive path and connector pad is illustrated. Pin 30, as illustrated, is first provided with an elongated layer 34 for each conductor in the lead to promote adhesion of the subsequently deposited conductive paths. Whether this layer is necessary will depend on the particular ceramic chosen for pin 30. This layer may conveniently consist of ceramic paste. Printed over layer 34 is a conductive path 38 which may be fabricated of platinum or gold. Following this, an additional insulative layer of ceramic paste 42 is applied over conductive path 38. Insulative layer 42 does not extend the full length of the conductive path 38 so that it is exposed at both its proximal and distal ends. The exposed proximal end of conductive path 38 serves as a connector pad for coupling to conductor 12. Finally, conductive pad 46 is applied over the distal end of conductive path 38. As illustrated, conductive pad 46 overlaps the distal end 43 of insulative layer 42. Conductive pad 46 engages with conductive, resilient rings within the connector block. Any convenient number of corresponding conductive paths and connector pads may be applied, to provide for a connector pin which provides for one, two, three or more connector surfaces. In the illustrated embodiment, one additional conductive path and connector pad is provided, coupled to coiled conductor 14.

As installed in the lead, the distal end 50 of conductor 12 is stripped of insulation and extended longitudinally, parallel to the axis of the lead. It is soldered or otherwise electrically coupled to the exposed proximal end of conductive path 38 thereby coupling it to the connector pad 46. Coiled conductor 14 is similarly coupled to the proximal end of a second corresponding conductive path, not visible in this illustration.

FIG. 2 shows a side, cut-away view of a connector block with the connector pin assembly of the lead illustrated in FIG. 1 inserted. In this view, the second connector pad 48 and insulative layers 36 and 44 are visible. These elements correspond to connector pad 46 and insulative layers 34 and 42, illustrated in FIG. 1. For use with a connector block as illustrated, connector pads 46 and 48 are displaced linearly from one another along the length of pin 30. The connector block includes a molded connector housing 100 which is provided with a lumen having a first, generally cylindrical portion 102 and a second, generally cylindrical portion 104, of smaller diameter and concentric to cylindrical lumen 102. The smaller diameter lumen 104 serves to align the proximal end of the ceramic pin 30 and keep it centered within lumen 102. Mounted within lumen 102 are a plurality of elastomeric rings including conductive elastomeric rings 106 and 108 and including nonconductive elastomeric rings 110, 112, 114 and 116. Conductive rings 106 and 108 may be fabricated of a conductive polymer, or of a polymer impregnated with a conductive material, such as silicone rubber impregnated with platinum, carbon or silver. Nonconductive rings 110, 112, 114 and 116 may be fabricated of silicone rubber or other appropriate elastic insulative plastic. The outer diameters of rings 106, 108, 110, 112, 114 and 116, in their relaxed states, should be slightly larger than the inner diameter of lumen 102 to facilitate frictional retention and fluid sealing of the rings within the lumen. The inner diameter of rings 106, 108, 110, 112, 114 and 116, when installed into lumen 102, should be slightly less than the outer diameter of pin 30 to facilitate both mechanical connection and fluid sealing. The use of resilient, non-metallic connectors is believed particularly advantageous in conjunction with ceramic connector pin 30, in that it substantially reduces the chances for damage to the connector pin by scratching or otherwise damaging the conductive and insulative layers printed thereon.

Connector housing 100 is also provided with a plurality of bores 118 and 120, perpendicular to lumen 102, and in communication with lumen 102. Additional bores could be provided in the event that a connector system employing more than two conductors is desired. As illustrated, connector housing 100 is mounted to the outer metallic enclosure 122 of a pacemaker, after insertion of rings 106-116. The outer enclosure 122 of the pacemaker is provided with feedthroughs 124 and 126. Feedthroughs 124 and 126 allow for passage of feedthrough wires 128 and 130. When installed on the outer enclosure 122 of the pacemaker, feedthrough wires 128 and 130 extend through bores 118 and 120 to make contact with the conductive resilient rings 106 and 108.

This connection system allows for extraordinary flexibility in the fabrication of connector blocks. For example, a unipolar pacemaker would employ only a single feedthrough. The connector block as illustrated could be installed on a unipolar pacemaker. Only one feedthrough wire would extend through into the lumen to make contact with a conductive elastomeric ring. Alternatively, a connector housing 100 could be fabricated with three or more linearly arranged perpendicular bores such as 118 and 120, allowing for use of the same connector housing with pacemakers having any equal or lesser number of feedthroughs extending from the outer enclosure 122.

FIG. 2 illustrates how conductive elastomeric rings 106 and 108 contact connector pads 46 and 48, respectively. However, a lead having a connector pin similar to ceramic pin 30, but bearing only a single connector pad, could similarly be inserted into the lumen 102 of connector housing 100, but would be electrically coupled to only one of the conductive rings 106 or 108. Alternatively, leads bearing connector pins such as connector pin 130 but having three or more connector pads would also be insertable into connector housing 100. Unused connector pads would be located adjacent one or more of the nonconductive resilient rings 110, 112, 114 and 116. This allows for implantation of a lead having three or more conductors, which would still be compatible for use with a pulse generator only having one or two feedthroughs to the connector block. This would result in disabling of whatever functions were coupled to the unused conductors on the pacing lead and would allow for upgrading of the system at a later time without the necessity of installing a new lead.

Overall, the combination of the connector pin 30 and the connector housing 100 with its installed resilient rings provides an interconnection system of unprecedented flexibility and manufacturing simplicity. It is also believed that the features of connector pin 30 and of connector housing 100 and its associated resilient rings would be individually applicable to other connector blocks and connector pin configurations.

Connector pin 30 is retained within the connector housing 100 by means of retainer 132. Retainer 132 is a generally cylindrically shaped, molded plastic part. The proximal end of retainer 132 displays a circular lumen 134 of a diameter slightly larger than connector pin 30, and is permanently mounted in lumen 102. This assembly serves both to retain the resilient rings 106 through 116 and to align connector pin 130 within lumen 102. Retainer 132 is provided with a plurality of beams 136 and 138, extending distally from connector housing 100. Each of the beams is provided with a bend, 140 and 142, which engages circumferential groove 26 of the tubular member 20. In their relaxed state, the curved portions 140 and 142 of beams 136 and 138 preferably display an inner diameter equal to the outer diameter of groove 26 to ensure a firm interlock while avoiding any cold flow of the plastic forming tubular member 20 or the retainer 132. The distal end 144 of the retainer takes the form of a cylinder, and ties the distal ends of the deflectable beams 136 and 138 together. This also increases the firmness of the mechanical interconnection between the deflectable beams and the circumferential groove 26 of cylindrical member 20. Although in the drawing illustrated, two deflectable beams 136 and 138 are shown, this is for purposes of illustration only. The inventors have determined that a system employing three or four deflectable beams may be preferable. A plan view of a retainer 132A employing three beams is illustrated in FIG. 3, below.

Surrounding retainer 132 is an insulative boot 146, which generally takes the form of a cylinder. Boot 146 may be fabricated of silicone rubber or other resilient, elastic material. Surrounding boot 146 in the vicinity of the curved portions 140 and 142 of beams 136 and 138 is a suture 150. This suture acts as a lock to prevent expansion of the deflectable beams 136 and 138 and removal of the connector pin 30 from the connector block 100. Because prior art pacemakers employ sutures in similar locations as fluid seals, the use of a suture as a connector lock does not represent additional work for the physician installing the pacemaker.

Figure 3:
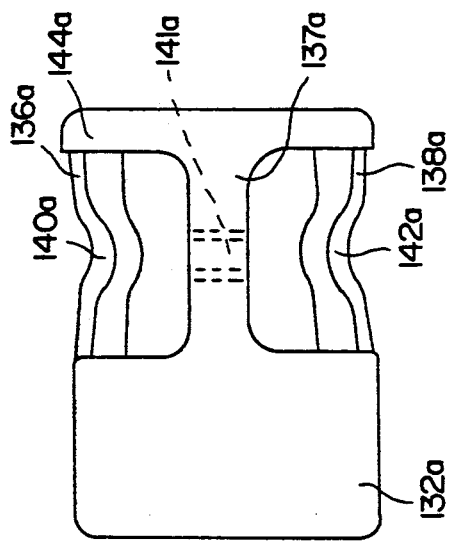
FIG. 3 is a plan view of the lead retainer used in conjunction with the connector block illustrated in FIG. 2.

FIG. 3 shows a plan view of a retainer 132A corresponding to the retainer 132 illustrated in FIG. 2. Numbered elements in FIG. 3 correspond to similarly numbered elements in FIG. 2. In this view, the apertures intermediate beams 136A, 137A and 138A, are visible. Each beam is provided with an inwardly, curved section 140a, 141a and 142a. The distal end 144a ties the distal ends of the beams together. Retainer 132A may be fabricated of Pellethane ® polyurethane, Delrin ®, polypropylene, or other relatively hard, elastic plastic.

Figure 4:
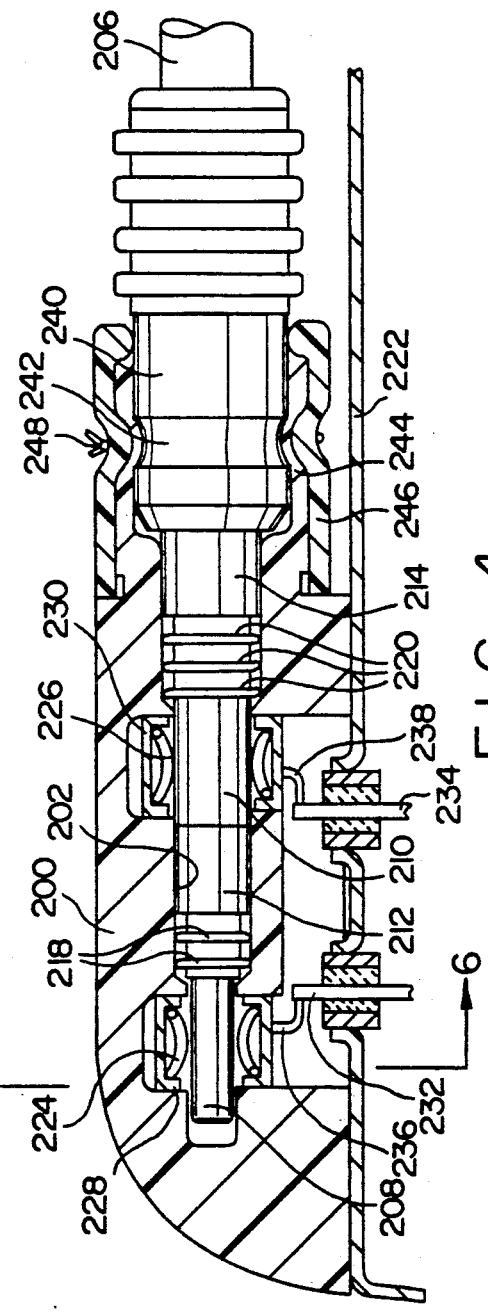
FIG. 4 is a cut-away view of a connector pin assembly and a connector block making use of a deflectable beam lead retainer, similar to that illustrated in FIGS. 2 and 3. The connector block also uses conductive spring members to contact the conductive surfaces on the connector pin.

FIG. 4 is a cut-away view of an alternative in-line connector block employing a lead retainer similar to that illustrated in FIGS. 2 and 3. The connector block 200 includes a stepped lumen 202, which receives the connector pin mounted to the proximal end of the pacing lead 206. The connector pin includes two conductive connector surfaces 208 and 210, and two insulative areas 212 and 214. Insulative areas 212 and 214 are each provided with a plurality of sealing rings 218, 220 which seal the lumen 202 against fluid entry and provide a seal intermediate conductive areas 208 and 210. Conductive area 208 takes the form of a metallic, cylindrical pin. Conductive area 210 takes the form of a metal cylinder. Connector block 200 is illustrated mounted to the outer enclosure 222 of an implantable pacemaker. Connection between the implantable pacemaker and the lead 206 is made by means of spring members 224 and 226, which are mounted in conductive ferrules 228 and 230, respectively. Ferrules 228 and 230 are metal cylinders having central bores and associated internal circumferential grooves which retain the spring members 224 and 226. When inserted, spring members 224 and 226 provide for electrical coupling. Ferrules 228 and 230 are coupled to feedthrough wires 232 and 234 by means of wires 236 and 238, respectively.

The proximal end of lead 206 is provided with a cylindrical plastic member 240, provided with a circumferential groove 242. This element corresponds to the cylindrical plastic member 20, illustrated in FIGS. 1 and 2. The distal end of the connector housing 200 is provided with a deflectable beam lead retainer 244, which corresponds to the deflectable beam lead retainers illustrated in FIGS. 2 and 3, above. In this particular embodiment, the retainer is shown as molded integral to connector block 200. However, alternate embodiments in which the retainer is fabricated separately and thereafter attached are also workable. Surrounding the deflectable beam retainer 244 is an insulative boot 244, corresponding to the insulative boot 22 illustrated in FIG. 2. Surrounding insulative boot 246 in the area of the circumferential groove 242 is a suture 248, which performs the same function as described in conjunction with suture 24, illustrated in FIG. 2 above.

Figure 5:
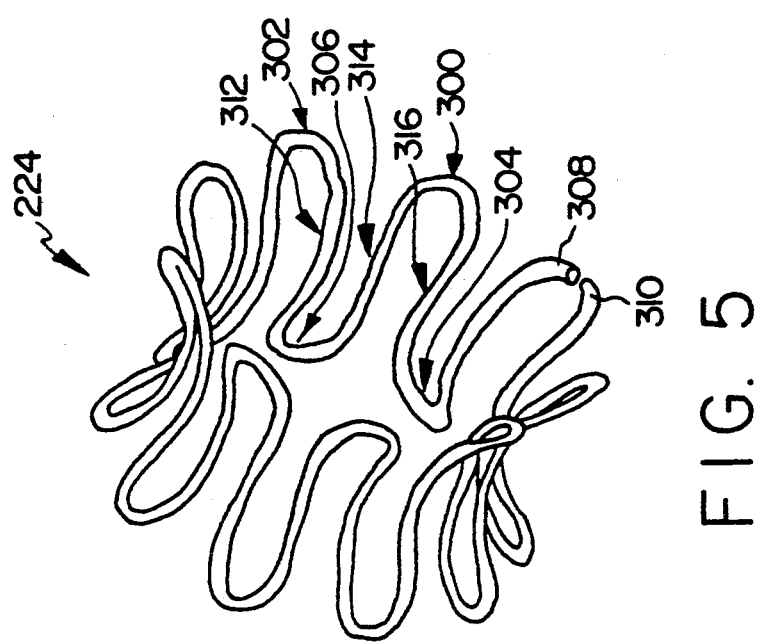
FIG. 5 is a plan view of a spring member used in the connector block illustrated in FIG. 4.

FIG. 5 is a plan view of spring member 224, illustrated in FIG. 4 above. The spring member 224 is fabricated from a single length of spring wire, provided with a plurality of bends, as illustrated at 300, 302, 304, 306, forming a zigzag pattern. The spring member is fabricated so that the portions of the wires 312, 314, 316 located intermediate the sharp bends (e.g. 300, 302, 304, 306) are arched. These arched sections of the spring member contact the connector surfaces on a cylindrical or other connector surface on a pacing lead. As fabricated, the spring member 224 generally has a planar configuration. When inserted into the ferrule 228, the spring member assumes the cylindrical configuration illustrated, with the arched portions, e.g. 312, 314, 316 directed inward. Although illustrated in FIG. 4 in conjunction with an in-line connector, these spring members are also usable in conjunction with bifurcated or other forms of pacing lead connectors.

Figure 6:
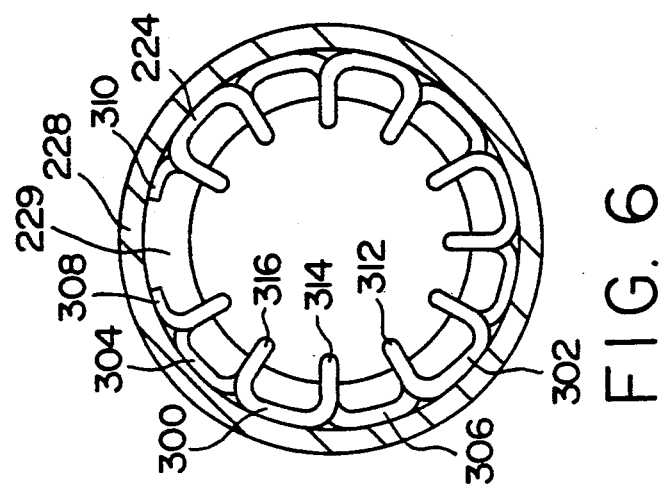
FIG. 6 is a cross sectional view of the spring member illustrated in FIGS. 4 and 5 and its associated cylindrical ferrule.

FIG. 6 illustrates the interrelation of the spring member 224 and its associated cylindrical ferrule 228. In this view, it can be seen that the sharp bends such as 300, 302, 304, 306 define the outer periphery of the spring member 224. The arched sections 312, 314, 316 define the inner surface of the spring member, and extend into the lumen of the ferrule 228. By providing a gap between spring member ends 308, 310, compression of the spring member and insertion into the ferrule is facilitated The spring member is retained within the ferrule by the end surfaces of the ferrule, of which only one, 229, is visible in this view. Preferably, the spring member 224 is sized so that when inserted, arched portions of the spring member, such as 312, 314 and 316, define an inner diameter through the ferrule of less than the outer diameter of connector surface 218, allowing for a good frictional fit. Because the arched portions 312, 314, 316 are deflected by connector surface 218, the groove within ferrule 228 must be somewhat wider than the spring member to allow for longitudinal expansion during compression of the spring member. By varying the degree of curvature on the arched portions, e.g. 312, 314, 316 of spring member 224, the force with which the spring member engages the connector pin may be varied.

It has been determined that garter springs, used in prior art pacemaker connector blocks as illustrated in U.S. Pat. No. 4,437,474, issued to Peers-Trevarton, cited above, undergo a complex, twisting motion during compression, making force applied by the spring difficult to model and to predict. The spring member illustrated in FIGS. 5 and 6, in contrast, is constructed so that it functions as a series of deflectable beam members. This provides for ready predictability of compressive force, allowing easy variation of material and other design parameters to accomplish the desired compressive force, and to vary it if necessary.

Although the connector pins, connector blocks, spring members, and lead retainers are all described as parts of integrated connector systems, these elements are also believed individually useful in other connector configurations. Although the embodiments illustrated both employ leads having two conductors coupled to pacemakers having two electrical feedthroughs, the inventions disclosed herein are believed to be equally applicable to connector systems having a greater or lesser number of connector surfaces involved.

In conjunction with the above description, we claim:

1. A method of manufacture of a connector block assembly for an electrical medical device of the type including one or more electrical conductors extending from said medical device, said method comprising:
   fabricating a connector block having a longitudinal lumen, said longitudinal lumen having an open distal end and one or more bores generally perpendicular to said longitudinal lumen, said bores open to an exterior face of said connector block and to the interior of said longitudinal lumen, the distance from said exterior face of said connector block to said longitudinal lumen being less than the distance which said one or more conductors extend from said medical device;
   inserting at least one conductive, non-metallic, resilient, ring shaped member having a central orifice into said longitudinal lumen through the distal end of said lumen such that said central orifice of said member is aligned with the longitudinal axis of said lumen, the outer diameter of said member corresponding to the diameter of said longitudinal lumen; and
   attaching said connector block to said medical device such that said at least one electrical conductor extends through at least one bore, into said longitudinal lumen of said connector block and into electrical contact with said at least one conductive ring shaped member.

2. A method according to claim 1, further comprising the additional step of inserting one or more ring shaped, non-metallic, non-conductive resilient members into said longitudinal lumen of said connector block adjacent said at least one conductive ring shaped member, and distal to said at least one conductive ring shaped member.

3. A method according to claim 6, wherein said step of fabricating said connector block comprises fabricating a connector block having at least two generally perpendicular bores open to said longitudinal lumen, and both exposed to said exterior face of said connector block and wherein said method comprises the additional step of insertion of at least two non-metallic resilient conductive ring shaped members, each having a central orifice, proximal and distal to said at least one non-conductive ring shaped member and each aligned with one of said at least two perpendicular bores.

4. A method according to claim 3, wherein said medical device is provided with at least two conductors extending from said medical device and wherein said step of attaching said connector block to said medical device comprises attaching said connector block such that each of said at least two conductors extends through a different one of said perpendicular bores and into contact with a different one of said conductive ring-shaped members.

5. A method of manufacture of a connector for an electrical medical device including one or more electrical conductors extending from said medical device comprising:
   fabricating a connector block having a longitudinal lumen having an open distal end and one or more bores generally perpendicular to said longitudinal lumen, said one or more bores each open to an exterior face of said connector block and to the interior of said lumen;
   inserting at least one conductive, non-metallic, resilient member having an orifice therethrough into said longitudinal lumen through the distal end of said lumen such that said orifice of said member is aligned with the longitudinal axis of said lumen, the outer periphery of said member corresponding to an internal surface of said longitudinal lumen; and
   attaching said connector block to said medical device such that said at least on electrical conductor extends through said at least one bore and into electrical contact with said at least one conductive member.

6. A method according to claim 5, comprising the additional step of inserting a non-conductive resilient member into said longitudinal lumen through the distal end of said lumen, said non-conductive member having an orifice therethrough and having an outer periphery corresponding to an internal surface of said longitudinal lumen, said non-conductive member inserted adjacent said conductive member, distal to said conductive member, and located such that the orifices of said conductive and non-conductive members are aligned.

7. A method of producing a connector pin, adapted to be coupled to a medical electrical lead for connecting said lead to a medical device, comprising:
   selecting an elongated insulative conductor pin;
   depositing first and second conductive paths extending longitudinally along said connector pin, said first and second conductive paths terminating in first and second conductive areas, respectively, circumferentially displaced from and electrically insulated from one another, deposited on the surface of said connector pin and coupled to said conductive paths; and applying an insulative layer to the exterior surface of said connector pin over said conductive paths, but not said conductive areas whereby electrical contact may be made with said conductive areas.

8. A method according to claim 7 wherein said step of depositing said second conductive path and conductive area comprises depositing a conductive path and conductive area which terminate distal to said first conductive area.

9. A method according to claim 7 or claim 8 wherein said connector pin is a circular, cylindrical connector pin.

10. A method according to claim 7 or claim 8 wherein said first and second conductive paths are linear.

11. A method according to claim 7 or claim 8 wherein said method further comprises coupling said connective paths on said connector pin to electrical conductors within said medical electrical lead.

* * * * *

UNITED STATES PATENT AND TRADEMARK OFFICE
CERTIFICATE OF CORRECTION

PATENT NO. : 5,070,605
DATED : December 10, 1991
INVENTOR(S) : Terry D. Daglow, and Richard D. Sandstrom It is certified that error appears in the above-indentified patent and that said Letters Patent is hereby corrected as shown below:

Column 8, Line 11, delete "claim 6", and insert in its place --claim 2--.

Signed and Sealed this

Sixth Day of September, 1994

Attest:

BRUCE LEHMAN

Attesting Officer     Commissioner of Patents and Trademarks